United States Patent
Vanlaer et al.

(10) Patent No.: US 9,420,784 B2
(45) Date of Patent: Aug. 23, 2016

(54) BIOCIDAL COMPOSITION AND METHOD FOR TREATING WATER OR SURFACES IN CONTACT WITH WATER

(71) Applicant: BLUECO BENELUX BV, Hilversum (NL)

(72) Inventors: Antoine Vanlaer, Paris (FR); Jean Guezennec, Plouzane (FR); Francois Ghillebaert, Affringues (FR)

(73) Assignee: BLUECO BENELUX BV, Hilversum (NL)

(*) Notice: Subject to any disclaimer, the term of this patent is extended or adjusted under 35 U.S.C. 154(b) by 0 days.

(21) Appl. No.: 14/774,888

(22) PCT Filed: Mar. 13, 2014

(86) PCT No.: PCT/FR2014/050589
§ 371 (c)(1),
(2) Date: Sep. 11, 2015

(87) PCT Pub. No.: WO2014/140498
PCT Pub. Date: Sep. 18, 2014

(65) Prior Publication Data
US 2016/0015030 A1      Jan. 21, 2016

(30) Foreign Application Priority Data
Mar. 14, 2013  (FR) ...................................... 13 52262

(51) Int. Cl.
  *A61K 31/04*  (2006.01)
  *A01N 33/04*  (2006.01)
  *A01N 25/00*  (2006.01)

(52) U.S. Cl.
  CPC ............... *A01N 33/04* (2013.01); *A01N 25/00* (2013.01)

(58) Field of Classification Search
  CPC .............................. A01N 33/04; A01N 25/00
  USPC .......................................................... 514/740
  See application file for complete search history.

(56) References Cited

U.S. PATENT DOCUMENTS

| | | | |
|---|---|---|---|
| 4,304,590 A | 12/1981 | Grade et al. | |
| 4,908,209 A | 3/1990 | McIntosh | |
| 5,108,504 A | 4/1992 | Johnson et al. | |
| 5,776,352 A * | 7/1998 | Vanlaer | A01N 33/04 106/18 |
| 2010/0029530 A1 | 2/2010 | Whiteley | |
| 2012/0164203 A1 | 6/2012 | Premachandran | |
| 2014/0056951 A1 | 2/2014 | Losick et al. | |
| 2014/0056952 A1 * | 2/2014 | Losick | A01N 33/04 424/400 |

FOREIGN PATENT DOCUMENTS

| | | |
|---|---|---|
| CA | 2 590 507 | 11/2008 |
| EP | 0 017 611 | 10/1980 |
| FR | 1601304 | 8/1970 |
| FR | 2 914 822 | 10/2008 |
| WO | 03/021111 | 3/2003 |
| WO | 2010/148158 | 12/2010 |
| WO | 2012/001164 | 1/2012 |
| WO | 2012/151555 | 11/2012 |

OTHER PUBLICATIONS

International Search Report dated May 9, 2014, corresponding to PCT/FR2014/050589.

* cited by examiner

*Primary Examiner* — T. Victor Oh
(74) *Attorney, Agent, or Firm* — Young & Thompson

(57) ABSTRACT

The present invention relates to a biocidal composition including at least one active biocidal compound and at least one nonionic or anionic exopolysaccharide (EPS), the active biocidal compound being selected from at least one triamine having the following formula I, $R^1NR^2R^3$, formula I where $R^1$ is an aminoalkyl radical comprising a straight or branched chain having 2 to 16 carbon atoms, R2 is a hydrogen atom or a straight or branched alkyl chain having 1 to 18 carbon atoms, and $R^3$ is, independently from $R^1$, an aminoalkyl radical comprising a straight or branched chain having 2 to 16 carbon atoms or a $-CH_2-CH_2-CH_2-NH-R_4$ radical, where $R_4$ is a saturated or unsaturated fatty acid chain including 4 to 20 carbon atoms or a mixture of $C_4$-$C_{20}$ alkyl chains, characterized in that the biocidal composition includes, by weight and relative to the total weight of said biocidal composition, 0.5 to 90% of the biocidal compound and 0.1 to 10% of the exopolysaccharide.

17 Claims, No Drawings

BIOCIDAL COMPOSITION AND METHOD FOR TREATING WATER OR SURFACES IN CONTACT WITH WATER

FIELD OF THE INVENTION

The present invention relates to the field of treating water and/or surfaces in contact with water.

In particular, the invention proposes a biocidal composition comprising a biocidal agent combined with a nonionic or anionic exopolysaccharide for the purpose of preventing the growth of and/or removing microorganisms and macroorganisms in water or on said surfaces in contact with water.

The invention also proposes a process for treating water and/or a surface in contact with water comprising said biocidal composition, and also the use thereof for treating industrial installations in which water circulates or is stored.

PRIOR ART

Many industries use either freshwater (water of streams, rivers, lakes, natural reservoirs or dams, drillings or wells), or salt water (seawater or brine). This water is used, for example, in firefighting water circuits, boiler water circuits, in cooling water circuits, in ship ballasts, or alternatively in offshore platforms or wind turbines. The water circulates in these industrial installations in ducts with an open or closed headspace. When the circulation takes place in an open circuit, the water is withdrawn, for example, from a river and is then discharged downstream, whereas when the water circulates in a closed and/or semi-closed circuit, the water is generally reused several times.

However, it is common for microorganisms to grow rapidly on the surfaces of these installations in which water circulates or is stored (aqueous or wet media), these microorganisms forming a biological or bacterial veil on these surfaces.

This biological veil, also known as a biofilm, consists of a community of microorganisms, especially such as bacteria, algae, protozoa and fungi which adhere together and to a surface. The production of biofilm is in fact characterized by the secretion of a matrix that is capable of adhering to numerous types of surfaces, especially mineral, metal, glass or synthetic resin surfaces.

The phenomenon of adhesion of an undesirable biofilm takes place in several sequences:

1. There is first formation of a primary film that conditions the surface. This primary film is formed from organic matter present in the medium.

2. Next, microorganisms become attached by reversible adhesion to the primary film (non-covalent or weak chemical bonds).

3. The adhesion of the microorganisms will then be permanent since it is facilitated by the production of saccharide exopolymers or of proteins or glycoproteins which constitute anchoring points for subsequent, more extensive, colonization of microorganisms. The film of permanently attached microorganisms on a surface constitutes the biofilm within the meaning of the present invention.

4. Finally, the colonization of a surface by a biofilm may bring about, in the long term, the attachment of macroorganisms belonging to the animal kingdom that may form large colonies. These macroorganisms may be molluscs such as mussels and oysters; serpulidae; crustaceans such as barnacles; hydroidea and bryozoa.

However, biological colonizations of microorganisms or macroorganisms, referred to hereinbelow as biofouling, may bring about numerous consequences both in the industrial field and in the environmental field.

For example, the presence of a biofilm in industrial installations may cause localized corrosions that are associated with the physical presence and metabolism of the microorganisms constituting this biofilm, whereas macroorganisms will form incrustations (deposits) on the surfaces of installations in contact with water. Now, these incrustations are difficult to remove and it is often necessary to stop the installation, empty out its water and then mechanically or manually remove said incrustations. Furthermore, the presence of this biofouling generally gives rise to a decrease in the flow rates of water (resistance to the throughput of fluids) and substantial losses of yield of industrial installations, for instance heat exchangers. Finally, the movement of live organisms in installations containing water, and especially in ship ballasts, may be the cause of the dissemination of invasive species, such as zebra mussels or of pathogenic species such as cholera virus.

In order to prevent and/or destroy this biofouling, several solutions have been proposed in the prior art.

Many "biocidal" compounds were first used for treating water.

These biocides usually comprise halogens or halogenated organic or mineral derivatives, such as chlorine, bromine, iodine, potassium chloride, hypochlorous acid and the sodium or calcium salts thereof, hypobromous acid, dichloro- and trichloroisocyanuric acid salts or halogenated hydantoins. However, these compounds have the drawback of being corrosive and of forming with the organic matter contained in water potentially toxic organohalogen compounds.

Other compounds have also been proposed, such as peroxygenated derivatives and phenolic derivatives, heavy metals or organic derivatives thereof, formaldehyde, benzoic acid and benzoates for treatments by injection or by contact with a coating. However, many of them leave toxic or corrosive residues or residues that biodegrade with difficulty in the treated water.

It is also known from the prior art that biocidal compounds may be used in solution or dispersion form in an aqueous phase optionally containing organic solvents. In this case, they are usually injected into the water to be treated. However, in certain cases, in particular when the surface to be protected is very small in comparison with the mass of water, they are incorporated into a material. This material may correspond, for example, to a paint that is applied to the surface to be protected, such as a boat hull, so as to treat the surface in contact with water.

To this end, FR-A-1 601 304 describes an algicidal coating comprising fatty monoamines and polyamines intended to be deposited onto the surfaces in contact with water that it is desired to protect. It is also known from EP-A-0 017 611 that fatty amines are capable of destroying microorganisms and, consequently, the biological veil. EP 0 716 045 also describes the use of several fatty amines for combating the growth of biological macrofouling in water or on surfaces in contact with water. FR 2 914 822 describes the use of a plant-protection composition comprising a triamine for neutralizing nematodes, bacteria or fungi.

Moreover, WO 2012/001164 describes the use of exopolysaccharide in order to prevent the adhesion of microorganisms to a surface.

It is also known from the prior art that biocidal agents may be used in combination with inert or texturizing polymers for various applications.

U.S. Pat. No. 5,108,504 describes, for example, ink compositions for inkjet printers, in which polysaccharides are used as texturizer and stabilizer at concentrations of between 0.05% and 0.75% by weight, optionally in the presence of from 0.1% to 0.4% by weight of a biocidal agent such as glutaraldehyde, which acts as a preserving agent.

U.S. Pat. No. 4,908,209 describes a biocidal composition which comprises a phosphate ester as biocidal agent and an inert vehicle in the form of a natural polymer (gelatin) or a synthetic polymer. The inert vehicle makes it possible to release the biocidal agent gradually over time.

Similarly, WO 2010/148158 presents a formulation (dispersion) comprising a biocide microencapsulated in an inert support (silicates, aluminosilicates, bentonite, diatomaceous earths). The formulation is stabilized with a thickener for improving the viscosity of the dispersion without modifying the original properties of the biocide. The thickener may be, for example, xanthan gum.

US 2010/029530 describes a detergent solution for decontaminating surgical instruments or other equipment, comprising a combination of a $C_8$-$C_{18}$ alkylpolysaccharide of a nonionic surfactant and a surfactant biocide containing nitrogen (such as 2-bromo-2-nitro-1,3-propanol or 2-methyl-4-isothiazolin-3-one).

CA 2 590 507 describes an antimicrobial composition for a cleaning substrate. The composition in particular comprises on a weight/weight basis: 3% to 50% of an antimicrobial agent such as a quaternary compound, 4% to 50% of a surfactant and 0.5% to 20% of a fragrance.

WO 03/021111 describes a process for treating running water and surfaces in contact with said running water, characterized in that at least one high molecular weight macromolecular compound with hydrodynamic friction-reducing properties and at least one monoamine or polyamine compound comprising an alkyl or alkenyl chain with biocidal properties are introduced into said water as a whole. The product is in the form of an emulsion.

WO 2012/151555 describes the use of a polyamine for inhibiting the formation of a biofilm.

There is thus a real need to develop alternative approaches to the conventional treatments in order to prevent the growth of and/or to remove microorganisms and macroorganisms in water or on said surfaces in contact with water.

In particular, there is an ongoing need to find novel biocidal compositions that can be conveniently used in an industrial installation in which water circulates in an open or closed circuit and which in particular have the following properties:
not inducing or ideally preventing the corrosion of surfaces in contact with water, whether this corrosion arises from biofouling or from chemical products contained in the water, such as $O_2$ or chlorides,
preventing the formation of the biological veil and the growth of colonies of macroorganisms,
leaving no toxic or corrosive residue in the water after use at a concentration that can destroy the flora and fauna downstream of the industrial installation and thus protecting the environment.

DETAILED DESCRIPTION OF THE INVENTION

The aim of the present invention is thus to propose a novel biocidal composition that avoids all or some of the abovementioned drawbacks.

To this end, one subject of the present invention is a biocidal composition comprising at least one biocidal active compound and at least one nonionic or anionic exopolysaccharide (EPS), the biocidal active compound being chosen from at least one triamine corresponding to formula I below:

$$R^1NR^2R^3 \qquad \text{Formula I}$$

in which $R^1$ represents an alkylamine radical (alkyl chain bearing an —$NH_2$ end group) comprising a linear or branched chain containing from 2 to 16 carbon atoms, $R^2$ represents a hydrogen atom or a linear or branched alkyl chain containing from 1 to 18 carbon atoms and $R^3$ represents, independently of $R^1$, an alkylamine radical comprising a linear or branched chain containing from 2 to 16 carbon atoms or a radical —$CH_2$—$CH_2$—$CH_2$—NH—$R^4$ in which $R^4$ is a saturated or unsaturated fatty acid chain comprising from 4 to 20 and preferably from 8 to 18 carbon atoms, such as a decyl, stearyl, oleyl, ricinoleyl, linoleyl, lauryl, myristyl, capryl or palmityl chain, or a mixture of $C_4$-$C_{20}$ and preferably $C_8$-$C_{18}$ alkyl chains, for instance copra, tallow or coconut chains, characterized in that the biocidal composition comprises, on a weight basis relative to the total weight of said biocidal composition: from 0.5% to 90% of the biocidal compound and from 0.1% to 10% of the exopolysaccharide.

The inventors have been able to develop a biocidal composition comprising a specific biocidal compound combined with a polysaccharide which is in particular an exopolysaccharide (EPS). Exopolysaccharides have no antimicrobial effect and have no biocidal activity either. However, surprisingly and unexpectedly, the inventors have discovered that exopolysaccharides made it possible to increase the biocidal activity of the biocidal composition according to the invention. Specifically, unexpectedly, the addition to the biocidal composition comprising the triamine of formula I of at least one exopolysaccharide made it possible to increase the biocidal activity of the composition with a synergistic effect.

Without wishing to be bound by any theory, the Applicant suggests that the biocidal composition of the invention interferes with the organic matter of the primary film or with the membranes of the live organisms (unicellular or pluricellular). In particular, it would appear that amphiphilic substances such as triamine composed of long hydrophobic chains and of a hydrophilic pole disrupt the biological membranes of these live organisms, which induces a modification in the transmembrane ion and gas transfers. This mechanism is thought to be due to the fact that the amphiphilic chains have a structure close to that of the phospholipids constituting this biological membrane.

In the context of the present invention, the term "primary film" means a conditioning film composed of proteins or protein fragments, carbohydrates, fats, mineral materials, for instance mineral salts, derived from the surrounding medium. This primary film stimulates the bacterial adhesion.

The term "biofilm" means a film of microorganisms, generally bacteria, which become attached to the primary film, in a first step of reversible and then irreversible adhesion. For the purposes of the present invention, a biofilm consists of microorganisms. Thus, the macroorganisms attached to a surface do not form a biofilm within the meaning of the present invention.

Also, unless otherwise specified, the indication of a range of values from "X to Y" or between "X and Y" in the present invention is understood as including the values X and Y.

The biocidal composition according to the invention is preferably an aqueous composition, defined as a product "containing active substances or containing preparations for destroying, repelling or rendering harmless harmful organisms (such as microorganisms or macroorganisms), for preventing their action or for combating them in any other manner by a chemical or biological action" (Article 2 of 89/8/EC Directive).

According to a first variant, a biocidal compound of formula I that is suitable for the biocidal composition of the present invention preferably corresponds to formula II below:

$$R-N{\Large\begin{array}{l}(CH_2)_3-NH_2\\(CH_2)_3-NH_2\end{array}}\quad\text{Formula II}$$

in which R is a linear or branched $C_1$-$C_{18}$, preferably $C_4$-$C_{16}$ and even more preferably $C_8$-$C_{14}$ alkyl chain.

The compounds of formula II that are suitable as biocidal compounds of the invention are advantageously chosen from: N,N-bis(3-aminopropyl)octylamine and N,N-bis(3-aminopropyl)dodecylamine, or a mixture thereof.

In particular, N,N-bis(3-aminopropyl)dodecylamine is preferred (EINECS No.: 219-145-8 and CAS No.: 2372-82-9). This compound is sold, for example, by the company Akzo-Nobel under the brand names Triameen® Y12D and Triameen® Y12D-30 or by the company Lonza under the brand name Lonzabac® 12.30.

According to a second embodiment variant, a biocidal compound of formula I that is suitable for the biocidal composition of the present invention preferably corresponds to formula III below:

$$R^5NH-CH_2CH_2CH_2NH_2\quad\text{Formula III}$$

in which $R^5$ represents the radical —$CH_2$—$CH_2$—$CH_2$—NH—$R^4$ in which $R^4$ is, as indicated above, a saturated or unsaturated fatty acid chain comprising from 4 to 20 and preferably from 8 to 18 carbon atoms, such as a decyl, stearyl, oleyl, ricinoleyl, linoleyl, lauryl, myristyl, capryl or palmityl chain, or a mixture of $C_4$-$C_{20}$ and preferably $C_8$-$C_{18}$ alkyl chains, such as copra, tallow or coconut chains.

The compounds of formula III that are suitable for use as biocidal compound of the invention are advantageously chosen from: N1-stearyldipropylenetriamine, N1-oleyldipropylenetriamine (CAS No.: 28872-01-7), N1-cocoyldipropylenetriamine (CAS No.: 91771-18-5), N1-tallow-dipropylenetriamine (CAS No.: 61791-57-9), or a mixture thereof.

In particular, N1-cocoyldipropylenetriamine and N1-tallowdipropylenetriamine are preferred.

According to the invention, the biocidal compound of formula I represents, on a weight basis, from 0.5% to 90%, preferably from 5% to 30%, even more preferably from 9% to 25% and more precisely from 12% to 17% relative to the total weight of the biocidal composition.

The biocidal composition may also contain another biocidal compound that is different from the triamine of formula I and which is preferably water-soluble.

This other biocidal compound may correspond, for example, to:

biocidal products for human hygiene, for instance: benzethonium chloride; tetradonium bromide; chloroxylenol; silver nitrate; N,N'-(decane-1,10-diyldi-1(4H)-pyridyl-4-ylidene)bis(octylammonium) dichloride;

disinfectants used in the private sector and in the public health sector and other biocides such as benzyl benzoate; potassium dimethyldithiocarbamate; thiram; ziram; thiabendazole; salicylic acid; silver; copper; compounds of the quaternary ammonium ion, benzyl($C_{12-18}$ alkyl)dimethyls, salts with benzisothiazol-1,2-one-3(2H) 1,1-dioxide (1:1);

disinfectants for surfaces in contact with foodstuffs and animal feed, for instance N-(3-aminopropyl)-N-dodecylpropane-1,3-diamine; didecyldimethylammonium chloride; silver chloride; compounds of the quaternary ammonium ion, benzyl($C_{12-18}$ alkyl)dimethyls, chlorides; dichlorophene; compounds of the quaternary ammonium ion, ($C_{12-14}$ alkyl)[(ethylphenyl)methyl]dimethyls, chlorides;

liquid-protecting products used in cooling and manufacturing systems, for instance N-(3-aminopropyl)-N-dodecylpropane-1,3-diamine; disilver oxide; polyhexamethylene biguanide; 2-chloroacetamide; 4,5-dichloro-2-octyl-2H-isothiazol-3-one; dodecylguanidine, monohydrochloride; chlorotoluron; prometryne; benzothiazole-2-thiol; quaternary ammonium compounds (dialkyldimethyl (saturated and unsaturated $C_6$-$C_{18}$ alkyl, and sulfur alkyl, cocoyl alkyl and soybean alkyl) chlorides, bromides or methyl sulfates/DDAC; quaternary ammonium compounds (benzylakyldimethyl (saturated and unsaturated $C_8$-$C_{22}$ alkyl, and tallow alkyl, cocoyl alkyl and soybean alkyl) chlorides, bromides or hydroxides/BKC; compounds of the quaternary ammonium ion, $C_{8-10}$ dialkyl dimethyl, chlorides; compounds of the quaternary ammonium ion benzyl($C_{12-14}$ alkyl)dimethyl, chlorides;

antimolding products such as sodium lignosulfonate; polymer of N-methylmethanamine (Einecs 204-697-4 with (chloromethyl)oxirane (Einecs 203-439-8)/polymerized quaternary ammonium chloride; N-didecyl-N-dipolyethoxyammonium borate/didecylpolyoxethylammonium borate; 1,2-benzisothiazole-3(2H)-one; bis(3-aminopropyl)octylamine; 2,2',2"-(hexahydro-1,3,5-triazine-1,3,5-triyl)triethanol; compounds of the quaternary ammonium ion, cocoyldimethyl [[[[(carboxy-2 ethyl)(hydroxy-2 ethyl)amino]-2 ethyl]amino]-2 oxo-2-ethyl]alkyl, hydroxides, internal salts;

fluid-protecting products used in the transformation of materials such as lignin; compounds of the quaternary ammonium ion, benzyl($C_{12-18}$ alkyl)dimethyl, chlorides; bronopol; compounds of the quaternary ammonium ion, benzyl($C_{12-16}$ alkyl)dimethyl, chlorides;

antifouling products: zinc pyrithione; dichloro-N-[(dimethylamino)sulfonyl]fluoro-N-(p-tolyl)methanesulfenamide/tolylfluanide; dichlofluanide; copper thiocyanate; dicopper oxide; bis(1-hydroxy-1H-pyridine-2-thionato-O,S) copper; zineb; N'-tert-butyl-N-cyclopropyl-6-(methylthio)-1,3,5-triazine-2,4-diamine;

or other synthetic compounds such as N-cocoyl-1,3-diaminopropane or natural compounds such as zosteric acid; or a mixture thereof.

Among the other biocidal compound different from the triamine of formula I, zosteric acid is preferred.

According to the invention, the other biocidal compound different from the triamine of formula I represents, on a weight basis, from 0 to 30%, preferably from 0.1% to 10% and even more preferably from 0.5% to 8% and more precisely from 1% to 3% relative to the total weight of the biocidal composition.

In the context of the present invention, the term "nonionic or anionic polysaccharide" means a carbohydrate macromolecule formed by a sequence of a large number of elementary sugars.

The nonionic or anionic exopolysaccharides according to the invention are high molecular weight polymers that are composed of sugars or oses and are derived from bacterial fermentation, i.e. they are secreted by microorganisms which release them into the culture medium. According to one embodiment, they may be native, i.e. chemically unmodified, or, according to a second embodiment, the EPSs may be modified by depolymerization and/or integration of chemical groups and functions.

Preferably, the EPSs used in the context of the invention have a molecular mass of greater than 500 kDa, preferably greater than 800 kDa, more preferentially greater than 1000 kDa and even more preferentially greater than 2000 kDa.

According to one embodiment of the invention, the EPSs used in the present invention comprise neutral oses, acidic oses, amino oses, sulfates and/or proteins. Examples of neutral oses include, but are not limited to, glucose, rhamnose, mannose and galactose. Examples of acidic oses include, but are not limited to, uronic acids and especially glucuronic acid, galacturonic acid, hexuronic acid, such as the hexuronic acid of furan structure substituted on its carbon in position 3 with a lactyl residue. Examples of amino oses include, but are not limited to, N-acetylglucosamine and N-acetylgalactosamine.

In particular, the EPSs that are suitable for use in the invention may comprise more than 30%, preferably from 30% to 95% of neutral oses, in particular from 40% to 90% and even more preferentially from 45% to 88% of neutral oses, as number of oses relative to the total number of oses in the EPS.

Advantageously, the EPSs of the invention comprise from 1% to 70% of acidic oses, preferably from 5% to 60% and even more preferentially from 8% to 53% of acidic oses, as number of oses relative to the total number of oses in the EPS.

Preferentially, the EPSs that are suitable for use in the invention comprise less than 30% of amino oses, preferably less than 20% and even more preferentially less than 12% of amino oses, as number of oses relative to the total number of oses in the EPS.

The exopolysaccharides may also contain non-carbohydrate substituents, for instance acetate, pyruvate, succinate and phosphate.

According to another characteristic, the EPSs of the invention comprise less than 50 sulfate molecules per 100 oses, preferably less than 40 sulfate molecules and even more preferentially less than 35 sulfate molecules per 100 oses in the EPS.

Preferably, the EPSs comprise less than 50 proteins per 100 oses, preferably less than 40 proteins and even more preferentially less than 37 proteins per 100 oses in the EPS.

Preferably, the EPSs do not comprise any aminoarabinose, aminoribose, heptose and/or xylose.

Advantageously, the bacteria producing the exopolysaccharides that are suitable for use in the present invention are isolated from natural samples or obtained from existing collections.

The EPSs of the invention are those synthesized under controlled conditions (nutritional imbalance generated by a high carbon/nitrogen ratio due to a nutritional medium enriched in carbohydrates) during the fermentation of bacteria derived from atypical ecosystems (Antarctic continent, microbial carpets, coral reefs, etc.).

According to a first embodiment, the EPSs are chosen from: dextran (*Leuconostoc mesenteroides, Leuconostoc dextranicum* and *Lactobacillus hilgardii*), xanthan (*Xanthomonas campestris*), succinoglycan (*Alcaligenes faecalis* var *myxogenes, Sinorhizobium meliloti*), galactomannan (*Achromobacter* spp., *Agrobacterium radiobacter, Pseudomonas marginalis, Rhizobium* spp. and *Zooglea'* spp.) or a mixture thereof.

According to a second embodiment, these EPSs are chosen from: MO 203, MO 245, MO 169, MO 229, FAK 1657, RA 19, RA 29, CAM 023, CAM 025, CMA 036, CAM 064, CAM 015, CAM 090, COT A, MICB-03A, EPS GG, MI 550, TIK 650 and TE 7, or a mixture thereof.

According to this second embodiment, these EPSs may be synthesized via bacteria of the genus *Alteromonas, Pseudoalteromonas, Vibrio, Pseudomonas* or *Pyrococcus* in accordance with the taxonomy in force at the date of the present invention. Should the taxonomy be modified, a person skilled in the art could adapt the taxonomic modifications to deduce therefrom the EPSs of the invention.

The compositions relating to these EPSs according to the second embodiment are indicated in the following table:

| EPS Reference | Neutral oses[1] | Acidic oses[1] | Amino oses[1] | Sulfates[2] | Proteins[2] |
|---|---|---|---|---|---|
| MO 203 | 46 | 20 | 0 | 0 | 4 |
| MO 245 | 10 | 30 | 30 | 0 | 3 |
| MO 169 | 52 | 28 | 0 | 8 | 5 |
| MO 229 | 60 | 18 | 0 | 7 | 6 |
| FAK 1657 | 55 | 10 | 0 | 0 | 1 |
| RA 19 | 48 | 8 | 0 | 29 | 3 |
| RA 29 | 44 | 8 | 0 | 21 | 8 |
| CAM 090 | 38 | 38 | 2 | 2 | 5 |
| CAM 025 | 68 | 12 | 0 | 5 | 2 |
| CAM 023 | 64 | 13 | 0 | 0 | 5 |
| CAM 015 | 40 | 25 | 0 | 0 | 10 |
| CAM 036 | 42 | 14 | 10 | 0 | 8 |
| CAM 064 | 46 | 17 | 5 | 4 | 4 |
| COT A | 40 | 8 | 8 | 6 | 10 |
| MICB-03A | 45 | 7 | 8 | 0 | 15 |
| EPS GG | 90 | 5 | 0 | 0 | 2 |
| MI 550 | 44 | 18 | 0 | 8 | 5 |
| TIK 650 | 47 | 10 | 0 | 0 | 8 |
| TE 7 | 38 | 14 | 2 | 8 | 8 |

[1] the relative amounts are indicated in % of oses relative to the total number of oses in the EPS
[2] the relative amounts are indicated as the number of molecules per 100 oses in the EPS.

These EPSs are known from the prior art and described especially in the following publications:

(RA19): Raguénès G, Moppert X, Richert L, Ratiskol J, Payri C, Costa B. A novel exopolymer-producing bacterium, *Paracoccus zeaxanthinifaciens* subsp. *payriae*, isolated from a "kopara" mat located in Rangiroa, an atoll of French Polynesia. Curr Microbiol Volume 49:145-51 (2004).

(CAM 025, CAM 036, CAM 015, CAM 064, CAM 090, CAM 023): C. A. Mancuso Nichols, J. Guezennec, J. P. Bowman Bacterial Exopolysaccharides from Extreme Marine Environments with Special Consideration of the Southern Ocean, Sea Ice, and Deep-Sea Hydrothermal Vents: A Review. Marine Biotechnology Volume 7, 253-271 (2005).

(MO 203, MO 245, RA 19, RA 29, MI 550, TIK 650, TE7): Jean Guézennec, Xavier Moppert, Gérard Raguénès, Laurent Richert, Bernard Costa, Christelle Simon-Colin: Microbial mats in French Polynesia and their biotechnological applications. Process Biochemistry, Volume 46 16-22 (2011).

The preferred EPSs that are suitable for use in the present invention are chosen from: MO 203, MO 169, FAK 1657, xanthan and dextran, or a mixture thereof.

Preferably, the EPS of the invention may be functionalized and bear cationic and/or anionic charges.

According to the invention, the exopolysaccharide represents, on a weight basis, from 0.1% to 10%, preferably from 0.5% to 8%, even more preferably from 0.5% to 5% and more precisely from 1% to 4% relative to the total weight of the biocidal composition.

The biocidal composition according to the invention is prepared by mixing the various constituents, namely by mixing at least water, the biocidal compound and the polysaccharide of the invention.

A subject of the present invention is also a process for treating water and surfaces in contact with said water in order to prevent the growth of and/or to remove a biological veil, microorganisms and macroorganisms in water or on said surfaces in contact with water, characterized in that the process comprises the following step(s): the biocidal composition as described above is injected into the water and/or applied to said surfaces.

Thus, according to a first embodiment, the biocidal composition according to the invention is advantageously injected into water. According to this first embodiment, the biocidal composition is injected into water intermittently or continuously. In the first case (intermittent treatment), a dose necessary to obtain a concentration of between 0.01 and 20 ppm of the biocidal composition per liter of water may be suitable on the surfaces treated. In the second case (continuous treatment), daily injections of the biocidal composition so as to obtain a concentration of the order of 6 mg/l may prove to be sufficient. The necessary concentrations of the biocidal composition depend on the microorganisms and macroorganisms to be removed, on the size and nature of the surfaces in contact with water and on the flow rate of water and may be readily determined by a person skilled in the art. According to one variant of this embodiment, the active products of the biocidal composition (PS or EPS and biocidal product) may be injected separately into the water.

According to a second embodiment, the biocidal composition is incorporated into a material, for example a paint, so as to be able to be applicable to a surface to be protected. According to this embodiment, the biocidal composition as described above is mixed, for example, with a pulverulent filler, such as micronized silica, so as to obtain a pulverulent product that is then introduced into a paint in the same manner as a pigment. The subject of the invention is thus also a paint used for performing this variant of the process which comprises the biocidal composition according to the invention.

The process according to the invention using the biocidal composition thus makes it possible to prevent the growth of the biological veil due to microorganisms or macroorganisms or to destroy them when they are formed and to prevent corrosion due to the biological veil.

According to the present invention, the inventors have discovered that the triamines of formula I combined with a polysaccharide such as an exopolysaccharide not only had activity on the biological veil and on the microorganisms constituting this veil, but also on macroorganisms belonging to the animal kingdom which attach to the surfaces in contact with water, whether or not there is possibility of photosynthesis. These macroorganisms may be sepulidae, crustaceans (barnacles), hydroidea, bryozoa and more especially molluscs, for example mussels and oysters.

To simplify, this activity against macroorganisms will be referred to in the rest of the application by the term "molluscicide activity". It has thus been found that this "molluscicide" activity is particularly high when a biocidal compound of formula I and in particular a biocidal compound of formula II or III is mixed with a polysaccharide such as dextran. Specifically, there is a synergistic reaction between these two types of compounds (specific biocidal compounds of the invention and a polysaccharide) insofar as, in addition, the polysaccharides do not have any antimicrobial or biocidal activity.

The biocidal composition used according to the invention also makes it possible to prevent, in a known manner, the formation of the biological veil due to microorganisms or to destroy them when it is formed and to prevent corrosion due to this biological veil.

A subject of the present invention is thus also the use of a biocidal composition as described above for preventing the growth of and/or for removing a biological veil, microorganisms and/or macroorganisms in water or on said surfaces in contact with water.

In particular, the biocidal composition is intended to be used in firefighting water circuits, boiler water circuits, in cooling water circuits, in ship ballasts, or alternatively in offshore platforms or wind turbines.

EXAMPLES

Examples of formulation of biocidal compositions according to the invention are given below as nonlimiting illustrations, and will allow the invention to be understood more clearly. The concentrations of the constituents are given on a weight basis relative to the total weight of the illustrated biocidal compositions.

Example 1

| Chemical substances | % concentration (mass/ total composition mass) |
| --- | --- |
| N,N-bis(3-aminopropyl)dodecylamine | 15.0 |
| Dextran | 3.0-5.0 |
| Water | 80.0-82.0 |

Example 2

| Chemical substances | % concentration (mass/ total composition mass) |
| --- | --- |
| N,N-bis(3-aminopropyl)dodecylamine | 15.0 |
| Dextran | 1.0 |
| Zosteric acid | 1.0-3.0 |
| Water | 80.0-83.0 |

Example 3

| Chemical substances | % concentration (mass/ total composition mass) |
| --- | --- |
| N,N-bis(3-aminopropyl)dodecylamine | 15.0 |
| MO 203 | 2.0 |
| Water | 83.0 |

Example 4

| Chemical substances | % concentration (mass/total composition mass) |
|---|---|
| N,N-bis(3-aminopropyl)dodecylamine | 15.0 |
| MO 169 | 2.0 |
| Water | 83.0 |

Example 5

| Chemical substances | % concentration (mass/total composition mass) |
|---|---|
| N,N-bis(3-aminopropyl)dodecylamine | 15.0 |
| FAK 1657 | 1.5 |
| Eau | 84.5 |

These various compositions were tested and it was found that:
- they did not induce, or even prevented, corrosion on surfaces such as steel, copper, ceramic, glass and plastic,
- they also prevented the formation of the biological veil and the growth of colonies of macroorganisms, and
- they did not leave any toxic or corrosive residue in the water after use at a concentration that could destroy the flora and fauna downstream of the industrial installation tested and thus protected the environment.

Although the invention has been described in relation with a particular embodiment, it is quite clear that it is in no way limited thereto and that it comprises all the technical equivalents of the means described and also combinations thereof if these combinations fall within the context of the invention.

The invention claimed is:

1. A biocidal composition comprising at least one biocidal active compound and at least one nonionic or anionic exopolysaccharide (EPS), the biocidal active compound being chosen from at least one triamine corresponding to formula I below:

$$R^1NR^2R^3 \quad \text{Formula I}$$

in which $R^1$ represents an alkylamine radical comprising a linear or branched chain with 2 to 16 carbon atoms, $R^2$ represents a hydrogen atom or a linear or branched alkyl chain with 1 to 18 carbon atoms and $R^3$ represents, independently of $R^1$, an alkylamine radical comprising a linear or branched chain with 2 to 16 carbon atoms or a radical —$CH_2$—$CH_2$—$CH_2$—NH—$R^4$ in which $R^4$ is a saturated or unsaturated fatty acid chain with 4 to 20 carbon atoms or a mixture of $C_4$-$C_{20}$ alkyl chains, wherein the biocidal composition comprises, on a weight basis relative to the total weight of said biocidal composition: from 0.5% to 90% of the biocidal compound and from 0.1% to 10% of the exopolysaccharide.

2. The biocidal composition as claimed in claim 1, wherein the biocidal compound of formula I corresponds to formula II below:

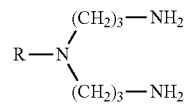

Formula II in which R is a linear or branched $C_1$-$C_{18}$ alkyl chain.

3. The biocidal composition as claimed in claim 2, wherein the biocidal compound of formula II is selected from the group consisting of: N,N-bis(3-aminopropyl)octylamine and N,N-bis(3-aminopropyl)dodecylamine, and a mixture thereof.

4. The biocidal composition as claimed in claim 3, wherein the biocidal compound of formula II is N,N-bis(3-aminopropyl)dodecylamine.

5. The biocidal composition as claimed in claim 1, wherein the biocidal compound of formula I corresponds to formula III below:

$$R^5NH—CH_2CH_2CH_2NH_2 \quad \text{Formula III}$$

in which $R^5$ represents the radical —($CH_2$—$CH_2$—$CH_2$—NH)—$R^4$ in which $R^4$ is a saturated or unsaturated fatty acid chain with 4 to 20 carbon atoms or a mixture of $C_4$-$C_{20}$ alkyl chains.

6. The biocidal composition as claimed in claim 5, wherein the biocidal compound of formula III is selected from the group consisting of: N1-stearyldipropylenetriamine, N1-oleyldipropylenetriamine, N1-cocoyldipropylenetriamine and N1-tallowdipropylenetriamine, and a mixture thereof.

7. The biocidal composition as claimed in claim 1, wherein the exopolysaccharide comprises more than 30% of neutral oses, from 1% to 70% of acidic oses and less than 30% of amino oses, as number of oses relative to the total number of oses in the EPS.

8. The biocidal composition as claimed in claim 7, wherein the EPS is selected from the group consisting of: dextran, xanthan, succinoglycan and galactomannan, and a mixture thereof.

9. The biocidal composition as claimed in claim 7, wherein the EPS is selected from the group consisting of: MO 203, MO 245, MO 169, MO 229, FAK 1657, RA 19, RA 29, MI 550, TE 7, TIK 650, CAM 023, CAM 025, CMA 036, CAM 064, CAM 015, CAM 090, COT A, MICB-03A, EPS GG, MI 550, TIK 650, TE 7, and a mixture thereof.

10. The biocidal composition as claimed in claim 1, wherein the biocidal compound of formula I represents, by weight, from 5% to 30% relative to the total weight of the biocidal composition and the exopolysaccharide represents, by weight, from 0.5% to 8% relative to the total weight of the biocidal composition.

11. A process for treating water and surfaces in contact with said water in order to prevent the growth of a biological veil and/or to remove a biological veil, microorganisms and macroorganisms in the water or on said surfaces in contact with the water, comprising injecting the biocidal composition as claimed in claim 1 into the water and/or applying to said surfaces.

12. The process as claimed in claim 11, wherein the biocidal composition is injected into the water intermittently.

13. The process as claimed in claim 11, wherein the biocidal composition is injected into the water continuously.

14. The process as claimed in claim 12, wherein at least the biocidal composition is mixed with a pulverulent filler, a paint is prepared using the mixture thus obtained as a pigment and said paint is applied to the surfaces in contact with water.

15. Method for preventing the growth of a biological veil and/or removing a biological veil, microorganisms an/or macroorganisms from water or on a surface in contact with water: which comprises treating said water or said surface in contact with water with an effective amount of the biocidal composition of claim 1.

16. The biocidal composition as claimed in claim 10, wherein the biocidal compound of formula I represents, by weight, from 9% to 25% relative to the total weight of the biocidal composition.

17. The biocidal composition as claimed in claim 10, wherein exopolysaccharide represents, by weight, from 0.5% to 5% relative to the total weight of the biocidal composition.

\* \* \* \* \*